United States Patent [19]

Panzani

[11] Patent Number: 4,859,333

[45] Date of Patent: Aug. 22, 1989

[54] CONTINOUS BLOOD CENTRIFUGATION CELL

[75] Inventor: Ivo Panzani, Mirandola, Italy

[73] Assignee: Dideco S.p.A., Mirandola, Italy

[21] Appl. No.: 177,722

[22] Filed: Apr. 6, 1988

[30] Foreign Application Priority Data

Apr. 7, 1987 [IT] Italy .................... 20038 A/87

[51] Int. Cl.⁴ ............... B01D 21/26; B04B 15/00
[52] U.S. Cl. .................. 210/360.2; 210/366;
210/369; 210/377; 210/379; 210/380.1; 494/38;
494/76
[58] Field of Search ............ 210/360.1, 360.2, 364,
210/367, 369, 377, 378, 379, 380.1, 382; 127/19;
494/38, 41, 43, 76, 77

[56] References Cited

U.S. PATENT DOCUMENTS 3,145,713 8/1964 Latham .......................... 494/41
3,409,213 11/1963 Latham .......................... 494/41
3,565,330 2/1971 Latham .......................... 494/41
4,300,717 11/1981 Latham .......................... 494/41

Primary Examiner—W. Gary Jones
Attorney, Agent, or Firm—Peter C. Richardson; Larry C. Akers; Roger C. Turner

[57] ABSTRACT

A continuous blood centrifugation cell includes a bell shaped outer container rotatable about a central axis, a coaxial inner volume displacement body which has a central longitudinal passage, and a circularly shaped partition which has a central aperture and which is coaxially enclosed between the body and the bottom of the container. A stationary housing is connected to and encloses the upper end of the container and has a coaxial inner conduit, a coaxial intermediate conduit, and a coaxial outer conduit. The housing has a stationary passage near the upper end of the container and is in communication with the lower end of the outer conduit for the removal of the lighter fraction blood components from the container. The intermediate conduit extends downwardly into the central passage of the body and has the lower end thereof closely spaced from the partition for the inlet of blood into the container. The inner conduit extends downwardly through the central passage of the body and through the central aperture of the partition with the lower end thereof closely spaced from the bottom of the container for the removal of the red blood corpuscles from the container. The cell also includes a sealing gasket within the aperture to seal the space between the inner conduit and the aperture to facilitate the removal of the red blood corpuscles through the inner conduit, during centrifugation.

4 Claims, 1 Drawing Sheet

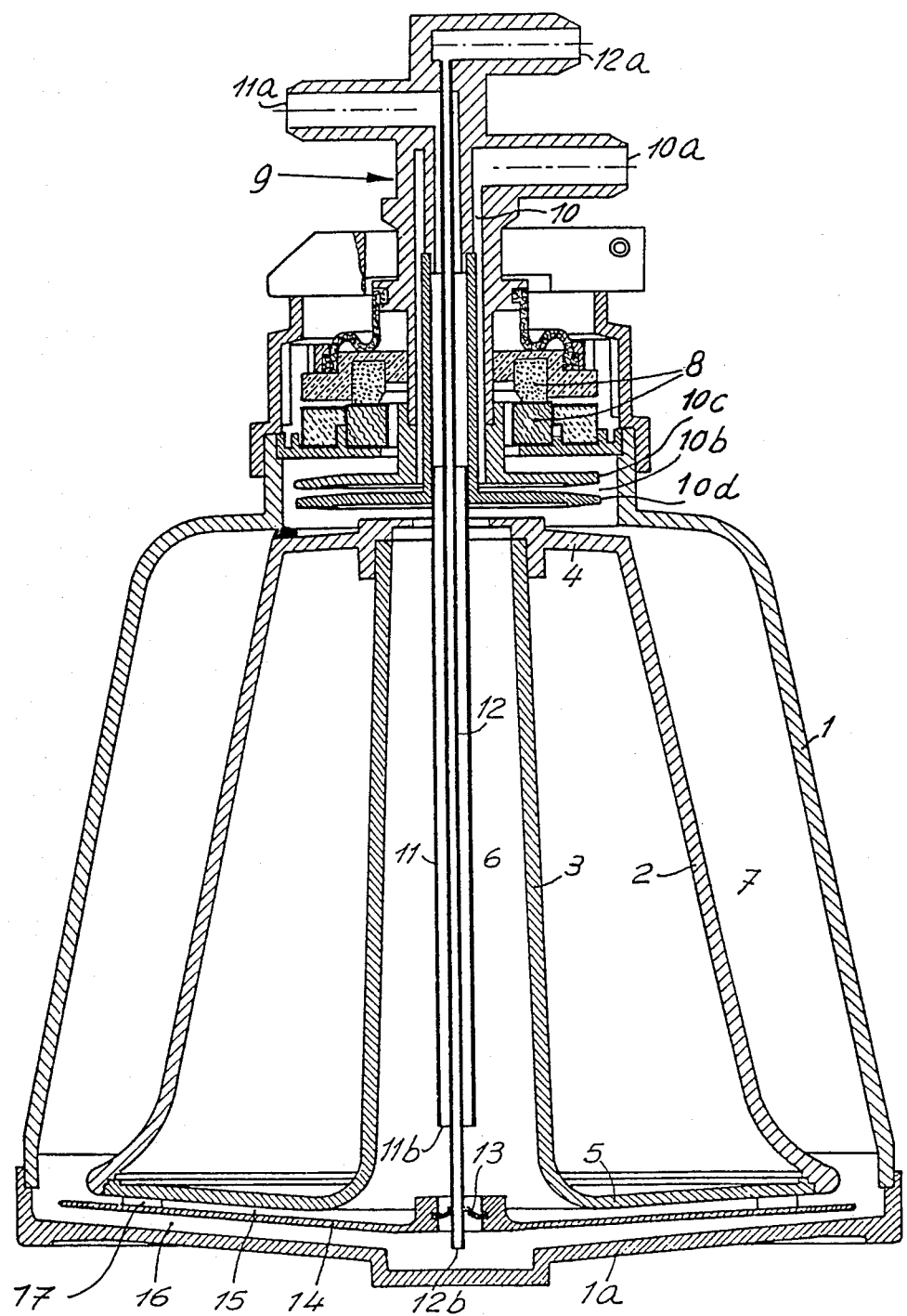

CONTINOUS BLOOD CENTRIFUGATION CELL

BACKGROUND OF THE INVENTION

The invention relates to a blood centrifugation cell, particularly a cell in which blood can be processed on a continuous basis for the withdrawal of red corpuscles without interruption of inflow or rotation. It is well known that blood centrifugation to achieve separation of the red corpuscles from the other blood components, such as plasma, white corpuscles and platelets, is currently achieved in devices known as cells or bowls. These cells usually include a bell-shaped (truncated-cone shaped) outer container of a desired volume. A somewhat smaller but similarly shaped volume displacement body having a central passage is coaxially enclosed within the container to facilitate separation. The body can be described as a solid of revolution having a cylindrical inner wall and a truncated conical outer wall which are hermetically sealed at the upper and lower edges of the walls. The cell includes a stationary housing which is connected to and which encloses the upper end of the container. The connection includes an annular, rotatable bearing with suitable gaskets and seals. The housing has two generally coaxial conduits extending into the container and adapted for external connections to tubing for the inflow of blood and the outflow of blood components. The central inner conduit extends through the central passage in the body and extends down to the bottom of the container. The outer conduit at its lower end, is in communication with an annular passage formed between two facing discs positioned at the base of the stationary housing, that is, in the space portion at the top of the container. In these known cells, the outer container is gripped and rapidly rotated by a rotating mandrel. The whole blood is fed into the cell through the inner conduit and reaches the bottom of the outer container where it is subject to a centrifugal force; as a consequence thereof, the red corpuscles, which are heavier, collect and concentrate against the wall of the outer container, separated at a substantially vertical front from the lighter fractions, constituted by plasma, platelets, and white corpuscles, which remain inwards.

As the process continues, the inflow of whole blood causes the level of the components separated in the container to rise, and at a certain point, the light components begin to enter the passage between the two discs of the stationary housing, then travel along the outer conduit and are evacuated. The process continues until the concentrated red corpuscles in the container causes the separation front to approach the passage between the discs of the stationary housing. At this point, the process must be interrupted to prevent the outflow of red corpuscles from the cell. The supply of whole blood is then interrupted and the mandrel rotating the cell is stopped. The cell is free of the lighter fractions and is full of concentrated red corpuscles which can be sucked through the central conduit to empty the cell and to be sent on to the intended use.

A distinct disadvantage of these known cells is that the extraction of the concentrated red corpuscles is possible only when these red corpuscles have completely filled the cell; and therefore only after a substantial amount of blood has been centrifuged. This disadvantage is particularly relevant in case of intraoperative autotransfusion, that is, recovery of blood spilled by a patient during surgery. This blood is sucked and combined with a physiological solution for washing, and sent to a cell for separation of the red corpuscles. It is vitally important to rapidly reinfuse the red corpuscles to the patient. With known cells, this rapid reinfusion is clearly impossible, since it is necessary for the cell to be completely filled with red corpuscles in order to stop blood separation and extract these red corpuscles. Use of small-volume cells does not solve the problem, since it is impractical to have a range of dimensions such as to optimized performance in the variety of actual case. The above description and disadvantages apply to the separation of red corpuscles from whole blood and also for separation of red corpuscles from the physiological solution.

SUMMARY OF THE INVENTION

It is an object of the present invention to provide a cell for centrifugation of blood which allows extraction of concentrated red blood corpuscles without having to wait for the cell to become completely filled.

It is another object of the invention to provide a cell which allows extraction of concentrated red blood corpuscles without having to discontinue rotation of the cell.

It is another object of the present invention to provide a cell for the extraction of red blood corpuscles without having to discontinue the inflow of whole blood or blood solution into the cell during extraction of red blood corpuscles.

It is still a further object of the invention to provide a cell having a particularly simple structure, such as to insure a minimum cost and a maximum reliability in operation.

These objects are achieved by a continuous blood centrifugation cell according to the present invention, which includes an outer container rotatable about a central axis which has an outer wall, an upper end, and a generally circularly shaped enclosed bottom. The cell includes a volume displacement body which has an upper end, a lower end, a generally cylindrical central longitudinal passage, and is coaxially enclosed within the container. The cell further includes a generally circularly shaped partition which has a central aperture and which is coaxially enclosed within and closely spaced from the bottom of the container and which has a diameter adapted to be closely spaced from the wall of the container. The cell includes a stationary housing which is connected to and which encloses the upper end of the container through an annular rotatable seal. The housing has a coaxial inner conduit, a coaxial intermediate conduit, and a coaxial outer conduit adapted for the inflow of blood and the outflow of blood components. A stationary passage is included within the housing near the upper end of the container and is in communication with the lower end of the outer conduit. The stationary passage and outer conduit are adapted for the removal of the lighter fraction blood components from the container. The intermediate conduit extends downwardly into the central passage of the body and has the lower end thereof closely spaced from the partition. The intermediate conduit is particularly adapted for the inlet of blood or blood solution into the container. The inner conduit extends downwardly through the central passage of the body and through the central aperture of the partition with the lower end thereof closely spaced from the bottom of the container. The inner conduit is particularly adapted for the removal of the red blood corpuscles from the container. The cell finally includes a sealing gasket within the aperture to seal the space between the inner conduit and the aperture to facilitate the removal of the red blood corpuscles through the inner conduit.

BRIEF DESCRIPTION OF THE DRAWING

Further features and advantages of the invention will become apparent from the detailed description of the invention described by way of a non-limitative example in the accompanying drawing wherein, FIG. 1 is a front elevational view in section illustrating the structure of the invention.

DETAILED DESCRIPTION OF THE INVENTION

The invention is better understood with reference to the figure in which a bell-shaped (truncated-conically shaped) outer container 1 has an outer wall, an upper end and an enclosed generally circularly (slightly convex exterior) shaped bottom 1a. The outer container encloses a volume displacement body 2 having an outer wall, an upper end 4, a generally circularly (slightly convex) shaped lower end 5 and a generally cylindrical central longitudinal passage 6. The body is somewhat smaller and has a shape substantially corresponding to the bell-shaped (truncated-conically shaped) configuration of the outer container 1 and is generally described as a solid of revolution having a cylindrical inner wall 3 and a bell-shaped outer wall 2 enclosed at the upper edges by the upper end 4 and at the lower edges by the lower end 5. The body is coaxially attached within the container with the lower end near (but not closely spaced from) the bottom 1a of the container and defines the central passage 6 and an outer passage 7 between the outer surface of the body and the inner surface of the wall of the container. The cell includes a generally circularly shaped partition 14 (corresponding to the shape of the bottom of the container) coaxially enclosed within the container and closely spaced from the bottom 1a of the container. The diameter of the partition is slightly less than the diameter of the bottom of the container so that the partition is closely spaced from the wall of the container. The lower end 5 of body 2 is preferably closely spaced from the partition 14 thereby creating a lateral passage 15 between the partition and the body and a bottom passage 16 between the partition and the bottom of the container whereby the passages 15 and 16 communicate with each other at the periphery of the partition. The passage 16, preferably includes a plurality of radial passages or channels formed in the bottom 1a of the container. In addition (or alternatively), passage 15 can include a plurality of radial passages or channels 17. The radial channels facilitate the flow of blood and the flow of the red corpuscles through the lateral passage 15 and bottom passage 16.

The cell includes a stationary housing, generally indicated as 9, which is connected through a set of annular rotatable seals and bearings, generally indicated as 8, to enclosed the upper end of the outer container 1. The housing includes three concentric conduits 10, 11 and 12 which are coaxial to the axis of rotation of the cell. The outer conduit 10 is provided with a tubing connection portion 10a at the upper end and communicates at its lower end with a passage 10b formed between two facing discs 10c and 10d located at the base of the housing near the upper end of the container. Passage 10b and conduit 10 are utilized primarily to remove the lighter fractions constituted by plasma, platelets, and white corpuscles from the cell. The intermediate conduit 11 extends downwardly into the central passage 6 of the body with the lower end 11b closely spaced from the partition 14. The intermediate conduit 11 is provided at the upper end with a typical tubing connection portion 11a and which acts as the inlet for whole blood or blood insulation into the cell.

A principle feature of the invention is the inner conduit 12. The inner conduit 12 extends downwardly through the central passage 6 in the body 2 and through the central aperture in the partition 14 with the lower end 12b thereof closely spaced from the bottom 1a of the container. The aperture of the partition includes a sealing gasket 13 which substantially seals the lower end 12b of the inner conduit within the bottom passage 16. Inner conduit 12 is provided at the upper end with a typical tubing connection portion 12a and this central inner conduit is primarily utilized to remove the red corpuscles from the container during centrifugation.

In operation of the centrifugation cell, the outer container 1 is retained by a mandrel and rapidly rotated by a rotating mandrel centrifuge device. Whole blood (or blood in solution) is continuously fed at connector 11a through intermediate conduit 11 and is discharged from the lower end 11b onto the partition 14 and is subject to the action of the centrifugal force as a consequence of the rotation of the container and enters the lateral passage 15. The red corpuscles concentrate against the wall of the outer container in outer passage 7 separated at a substantially vertical front from the light fractions which remain inwards. As the inflow of whole blood continues, the light fractions are received by the passage 10b and are extracted from the cell by way of conduit 10. In known cells, the centrifugation continues until the cell is completely filled with concentrated red corpuscles.

With the present invention, it is possible at any time to extract red corpuscles without the cell being completely filled, without interrupting rotation of the cell, and without interruption of the inflow of whole blood at the inlet. This is accomplished in the present invention by applying a vacuum or negative pressure at the external end 12a of inner conduit 12 which is in communication with the bottom passage 16 which is in peripheral communication with the outer passage 7 adjacent to the outer wall where the concentrated red corpuscles are located. The sealing gasket 13 separates this red corpuscle communication passage network from light fractions located (through central passages 6) in the upper and inner portions of the container. The extraction of red corpuscles can thereby be withdrawn through conduit 12 throughout the centrifugation process.

The position of the separation front between the red corpuscles and light fractions which obviously shifts during the operation according to the mutual variations of rates of inflow of whole blood and the outflow of red corpuscles is controlled either visually by an operator through a transparent outer container or by means of photocells to insure maximum effectiveness.

In the case of autotransfusion, after even a small amount of blood has been recovered and sent to the cell, it is possible to quickly perform reinfusion of the red corpuscles back to the patient.

The present invention thereby provides a continuous centrifugation cell which permits continuous extraction of red corpuscles without interruption of the inflow of whole blood or interruption of the rotation of the cell. This feature eliminates significant idle time for the efficient operation of the centrifugation cell.

Although the present invention has been described and illustrated in connection with a certain embodiment, it is to be understood that modifications and variations may be resorted to without departing from the spirit of the invention, as those skilled in the art will readily understand. Such modifications and variations are considered to be within the perview and scope of the present invention as defined by the appended claims.

What is claimed is:

1. A centrifugation cell for blood and biological liquids, comprising:
    an outer container rotatable about a central axis having an outer wall, an upper end and a generally circularly shaped enclosed bottom;
    a volume displacement body having an upper end, a lower end, a generally cylindrical central longitudinal passage therein, and coaxially enclosed within said container;
    a generally circularly shaped partition coaxially enclosed within and closely spaced from the bottom of said container and having a diameter adapted to be closely spaced from the wall of said container and having a central aperture therein;
    said lower end of said body being closely spaced from said partition;
    a stationary housing connected to and enclosing the upper end of said container through an annular rotatable seal and having a coaxial first conduit, a coaxial second conduit, and a coaxial third conduit;
    a means providing a stationary passage within said housing near the upper end of said container and in communication with said third conduit and adapted for the removal of lighter fraction blood components;
    said second conduit extending downwardly into the central passage of said body, with the lower end thereof closely spaced from said partition, and adapted for the inlet of blood into said container;
    said first conduit extending downwardly through the central passage of said body and through the central aperture of said partition with the lower end thereof closely spaced from the bottom of said container, and adapted for the continuous removal of the red blood corpuscles, and
    a means for substantially sealing the space between said first conduit and the aperture in said partition.

2. The centrifugation cell of claim 1 further comprising a plurality of radial passages between said partition and the bottom of said container.

3. The centrifugation cell of claim 1 further comprising a plurality of radial passages between said partition and the lower end of said body.

4. A centrifugation cell for blood and biological liquids, comprising:
    an outer container rotatable about a central axis having an outer wall, an upper end and a generally circularly shaped enclosed bottom;
    a volume displacement body having an upper end, a lower end, a generally cylindrical central longitudinal passage therein, and coaxially enclosed within said container;
    generally circularly shaped partition coaxially enclosed within and closely spaced from the bottom of said container and having a diameter adapted to be closely spaced from the wall of said container and having a central aperture therein;
    said lower end of said body being closely spaced from said partition;
    a stationary housing connected to and enclosing the upper end of said container through an annular rotatable seal and having a coaxial first conduit, a coaxial second conduit, and a coaxial third conduit;
    a means providing a stationary passage within said housing near the upper end of said container and in communication with said third conduit and adapted for the removal of lighter fraction blood components;
    said second conduit extending downwardly into the central passage of said body, with the lower end thereof closely spaced from said partition, and adapted for the inlet of blood into said container;
    said first conduit extending downwardly through the central passage of said body and through the central aperture of said partition with the lower end thereof closely spaced from the bottom of said container, and adapted for the continuous removal of the red blood corpuscles, and
    a means for substantially sealing the space between said first conduit and the aperture in said partition;
    said sealing means including an elastomeric gasket having a diameter adapted to engage the aperture of said partition and having an opening therein adapted to receive said first conduit.

* * * * *